(12) United States Patent
Shih

(10) Patent No.: US 11,684,051 B2
(45) Date of Patent: Jun. 27, 2023

(54) ROTATING DISC TYPE CONTINUOUS AUTOMATED BIOLOGICAL BREEDING APPARATUS

(71) Applicant: STONBO CREATIVE CO. LTD, Yilan County (TW)

(72) Inventor: Cheng-Jen Shih, Yilan County (TW)

(73) Assignee: STONBO CREATIVE CO. LTD, Yilan County (TW)

( * ) Notice: Subject to any disclaimer, the term of this patent is extended or adjusted under 35 U.S.C. 154(b) by 0 days.

(21) Appl. No.: 17/669,510

(22) Filed: Feb. 11, 2022

(65) Prior Publication Data

US 2022/0295766 A1    Sep. 22, 2022

(30) Foreign Application Priority Data

Mar. 19, 2021 (TW) ................................. 110202981

(51) Int. Cl.
*A01K 67/033* (2006.01)

(52) U.S. Cl.
CPC .................. *A01K 67/033* (2013.01)

(58) Field of Classification Search
CPC .................................................. A01K 67/033
See application file for complete search history.

(56) References Cited

U.S. PATENT DOCUMENTS

| | | | | |
|---|---|---|---|---|
| 3,862,029 A * | 1/1975 | Joyce | ..................... | G01N 15/04 209/208 |
| 2019/0194082 A1 | 6/2019 | Bakhsh | | |
| 2021/0137137 A1* | 5/2021 | Leo | ......................... | A23K 40/20 |

FOREIGN PATENT DOCUMENTS

| | | |
|---|---|---|
| CN | 111436401 A | 7/2020 |
| CN | 212325166 U | 1/2021 |
| CN | 112385609 A | 2/2021 |
| JP | 54155997 U | 10/1979 |
| JP | 8173945 A | 7/1996 |
| JP | 2001247388 A | 9/2001 |
| JP | 200933997 A | 2/2009 |

OTHER PUBLICATIONS

European Patent Office, Search Report dated Aug. 11, 2022 for EP application No. 22157719.0.

* cited by examiner

*Primary Examiner* — Monica L Perry
*Assistant Examiner* — Aaron M Rodziwicz
(74) *Attorney, Agent, or Firm* — Li & Cai Intellectual Property (USA) Office

(57) ABSTRACT

A rotating disc type continuous automated biological breeding apparatus includes a plurality of rotating disc type breeding boxes and a central rotating shaft. The rotating disc type breeding boxes are stacked on each other in a longitudinal direction to form a breeding tank. Each of the rotating disc type breeding boxes includes at least one pushing plate and a lower feeding port, and the at least one pushing plate is configured to divide one of the rotating disc type breeding boxes that corresponds to the at least one pushing plate into at least one breeding compartment. The central rotating shaft penetrates through the rotating disc type breeding boxes along the longitudinal direction. The pushing plate of each of the rotating disc type breeding boxes is fixedly connected to the central rotating shaft, and the central rotating shaft is configured to drive the pushing plate to rotate.

7 Claims, 4 Drawing Sheets

ROTATING DISC TYPE CONTINUOUS AUTOMATED BIOLOGICAL BREEDING APPARATUS

CROSS-REFERENCE TO RELATED PATENT APPLICATION

This application claims the benefit of priority to Taiwan Patent Application No. 110202981, filed on Mar. 19, 2021. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a biological breeding apparatus, in particular to a rotating disc type continuous automated biological breeding apparatus, which is suitable for automated continuous breeding of higher multicellular organisms or microorganisms, such as insects, earthworms, or microorganisms, in large quantity.

BACKGROUND OF THE DISCLOSURE

Conventional fermentation tanks of wineries are capable of carrying out fermentation and production of various types of alcohol in large quantities, but are limited to cultivation of yeasts or other microorganisms. Conventional bioreactors, on the other hand, can cultivate animal cells, and can be used in large-scale cultivation of cells in pharmaceutical factories for preparation of medicines.

The applicant of the present application has applied and obtained a utility model patent (Taiwan Patent Application No. TW11041209480) in 2021, titled "Tower Continuous Automatic Biological Breeder". This technology is essentially used to continuously and automatically breed black soldier flies and mealworms. Furthermore, the technology disclosed in said patent can be used to treat a large amount of organic waste (>500 kg per day), and can be used in households to treat a small amount of household food waste (<5 kg per day).

Due to the increase in population and the relative shortage of protein, insect proteins, such as that from black soldier flies (*Hermetia illucens*) or mealworms (*Tenebrio molitor*), have gradually replaced proteins such as soybeans or fish meal for feed formulation. The black soldier flies can be bred using organic wastes, such as kitchen waste or poultry and livestock manure; therefore, they can be used to digest the organic wastes so as to replace other ways of waste treatment such as incineration or landfills, and reduce environmental pollution. Furthermore, the black soldier flies can convert the organic wastes into insect proteins as feed, and the feces of the black soldier flies can be used as organic fertilizer. The breeding of black soldier flies for such purposes is an important discovery for ecological recycling, resource recovery, energy saving and carbon reduction, and can contribute to the goal of achieving zero carbon emission by year 2050.

In recent years, numerous devices for breeding black soldier flies or other insects in large quantities has been developed, but most of them require large investments, complex devices, expansive area, and high energy consumption, so that the concept of using insects to treat and convert organic wastes into insect proteins and organic fertilizers can only be considered by a few large corporations.

Various types of organic wastes include livestock manure from livestock farms, offal waste from slaughterhouses, scraps from food factories, or kitchen waste from households or communities. Total amounts of the organic wastes generated by different sources can vary greatly. The organic wastes require a more suitable and adaptable treatment manner for an on-site and immediate treatment, so as to avoid long-distance transportation and energy consumption. In addition, such immediate treatment can reduce environmental pollution.

SUMMARY OF THE DISCLOSURE

In response to the above-referenced technical inadequacies, the present disclosure provides a rotating disc type continuous automated biological breeding apparatus, which is suitable for being used in a large quantity automated continuous breeding of higher multicellular organisms or microorganisms, such as insects, earthworms, or microorganisms, etc.

In one aspect, the present disclosure provides a rotating disc type continuous automated biological breeding apparatus including a plurality of rotating disc type breeding boxes and a central rotating shaft. The plurality of rotating disc type breeding boxes are stacked on each other in a longitudinal direction to form a breeding tank. Each of the rotating disc type breeding boxes includes at least one pushing plate and a lower feeding port, and the at least one pushing plate is configured to divide one of the rotating disc type breeding boxes that corresponds to the at least one pushing plate into at least one breeding compartment. The central rotating shaft penetrates through the plurality of rotating disc type breeding boxes in the longitudinal direction. The at least one pushing plate of each of the rotating disc type breeding boxes is fixedly connected to the central rotating shaft, and the central rotating shaft is configured to drive the at least one pushing plate to rotate in a first rotation direction through a motor or a pedal. A top-layer breeding box of the plurality of rotating disc type breeding boxes is configured to receive organisms to be cultivated. When the central rotating shaft drives the at least one pushing plate of each of the rotating disc type breeding boxes to rotate, the organisms located in the top-layer breeding box are pushed by the at least one pushing plate into the at least one breeding compartment of a second-layer breeding box of the plurality of rotating disc type breeding boxes below the top-layer breeding box through the lower feeding port of the top-layer breeding box, and then the organisms are pushed into the at least one breeding compartment of a third-layer breeding box of the plurality of rotating disc type breeding boxes below the second-layer breeding box through the lower feeding port of the second-layer breeding box until the organisms are pushed into a bottom-layer breeding box of the plurality of rotating disc type breeding boxes, so as to complete a cultivation process of the organisms.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
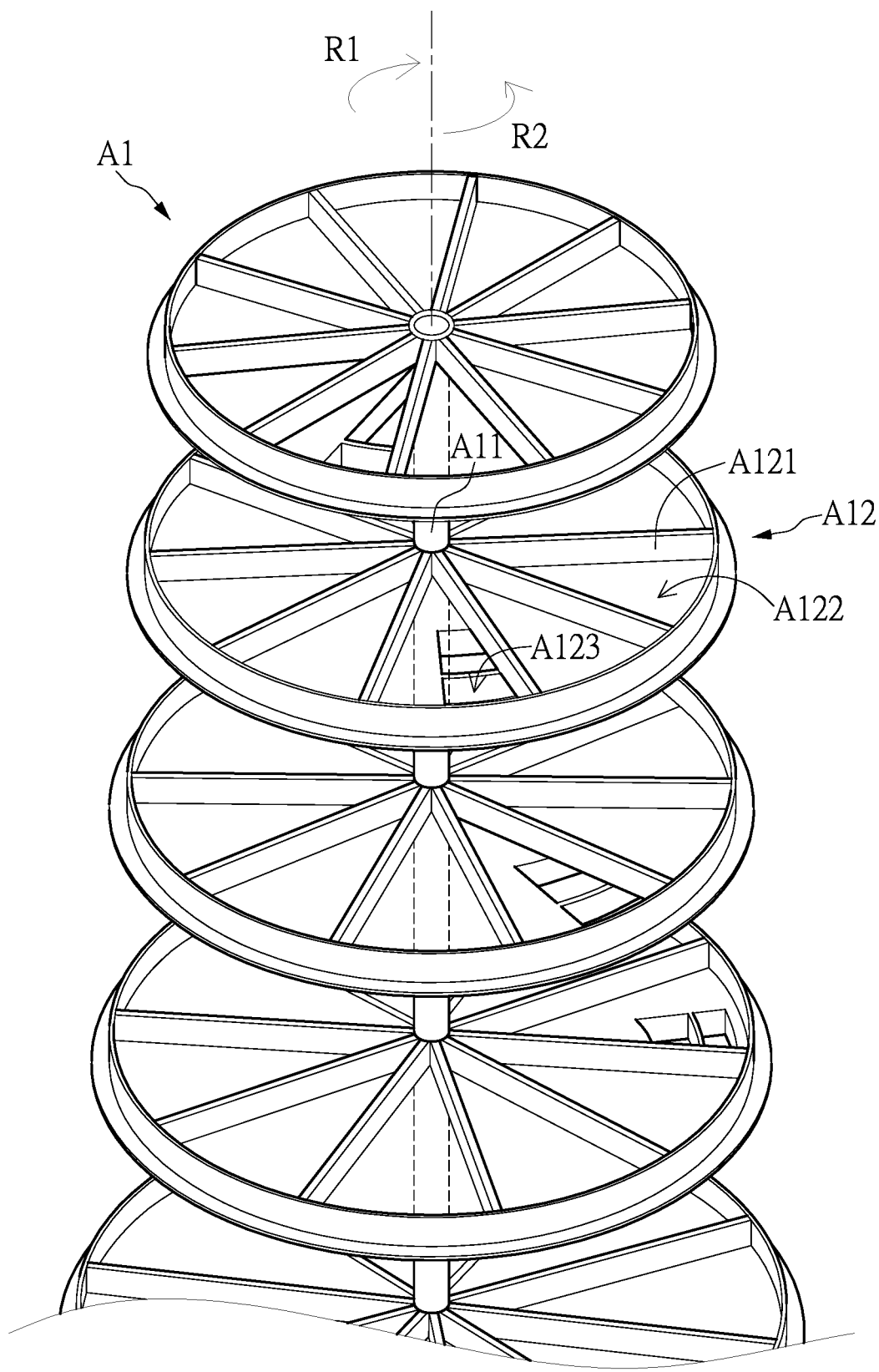
FIG. 1 is a perspective view of a plurality of rotating disc type breeding boxes according to a first embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

[Rotating Disc Type Continuous Automated Biological Breeding Apparatus]

The concept of the present disclosure is mainly derived from large-scale fermentation tanks or bioreactors. In addition to breeding multicellular organisms such as insects, earthworms, etc., to treat organic waste, the present disclosure is also suitable for fermentation of microorganisms in a large quantity to produce compost and the like.

The present disclosure provides a rotating disc type continuous automated biological breeding apparatus, the technical concept of which mainly includes four parts. A first part provides a rotating disc type breeding tank, which includes a plurality of rotating disc type breeding boxes. The plurality of rotating disc type breeding boxes are stacked on each other in a longitudinal direction and organisms of different growth days can be separated in the rotating disc type breeding tank. A second part is that, an inside of a box body of each of the rotating disc type breeding boxes is fixed to a central rotating shaft of the rotating disc type breeding tank via at least one pushing plate. Each of the pushing plates divides the rotating disc type breeding tank into a plurality of breeding compartments. A third part provides a large-scale food waste processor. The large-scale food waste processor includes a plurality of rotating disc type breeding boxes that have different diameters and sizes and stacked in a conical shape in the longitudinal direction. Among them, a bottom-layer breeding box of the plurality of rotating disc type breeding boxes has a maximum diameter, and a top-layer breeding box of the plurality of rotating disc type breeding boxes has a minimum diameter. In a special case, such as when the diameter of the rotating disc type breeding box exceeds 3 meters, each of the pushing plates has a consolidated outer ring and ribs mounted at an interval of one meter away from the central rotating shaft. In this way, the axial torsion can be dispersed, and the pulling force of the pushing plate can be strengthened. A fourth part provides a small-scale food waste processor. The small-scale food waste processor includes a plurality of rotating disc type breeding boxes that have the same diameters. At least one pushing plate is installed inside each of the rotating disc type breeding boxes. The at least one pushing plate is connected to the central rotating shaft of the rotating disc type breeding tank. Furthermore, the small-scale food waste processor uses a spiral feeding tube to send crushed food waste from an upper layer to the breeding boxes of each layer. The rotating disc type continuous automated biological breeding apparatus of the present disclosure can be used to breed various organisms, such as black soldier flies, house flies, mealworms, crickets, *Spodoptera litura*, silkworms, cockroaches, soil beetles, lacewings, rice worms, beetles, earthworms, microorganisms, aquaculture organisms, or other creatures capable of being used for bred or being consumed by natural enemies. The rotating disc type continuous automated biological breeding apparatus of the present disclosure can also be used as a layered continuous fermentation tank to mass-produce microorganisms such as fungi, bacteria, and the like. The rotating disc type continuous automated biological breeding apparatus of the present disclosure is mainly used to process organic waste such as kitchen waste, fruit and vegetable residues, distiller grains, bean dregs, tea residues, coffee residues, poultry and livestock manures, slaughterhouse waste, animal carcasses, food factory waste, sludges, biogas muds, and other organic wastes.

Overall, the present disclosure provides a rotating disc type continuous automated biological breeding apparatus that has a plurality of rotating disc type breeding boxes designed according to living habits of organisms. The plurality of rotating disc type breeding boxes can be vertically stacked to reduce a horizontal breeding space. Each layer of the breeding boxes is divided by at least one pushing plate to form at least one breeding compartment for the growth and development of organisms in the breeding compartment. Each layer of the breeding boxes has a lower feeding port. The lower feeding port works in cooperation with the rotation of the pushing plate to push smaller organisms in the upper breeding box of an upper layer through the lower feeding port into the breeding box of a lower layer. In this way, each layer of the breeding boxes can breed organisms of different growth periods. In the early stage, the smaller organisms are placed in the uppermost breeding box. As the breeding time elapses, the organisms in the uppermost breeding boxes are pushed down to the lowermost breeding boxes layer by layer through middle layers until the organisms are mature for harvest. In addition, the present disclosure also applies relevant supporting breeding technologies such as feeding, supplying, ventilation, and post-harvest processing, so that the breeding apparatus can continuously and automatically breed various organisms in a large quantity, thereby simplifying the breeding apparatus, saving energy, reducing costs, and reducing space. Furthermore, organic wastes, such as kitchen waste, peel residues, and poultry and livestock manure, can be treated to enhance the recycling of resources.

The breeding apparatus of the present disclosure has advantages of having a simple structure, and a size of the breeding apparatus can be adjusted according to the amount of organic waste to be processed. A large-scale breeding apparatus can be installed in garbage collection sites or large-scale livestock farms to achieve the purpose of processing a large amount of organic waste. In addition, a small-scale breeding apparatus can be installed in kitchens of a community or household. In this way, the purpose of on-site and immediate disposal of food waste and organic waste can be achieved.

[Large-Scale Biological Breeding Apparatus]

Figure 2:
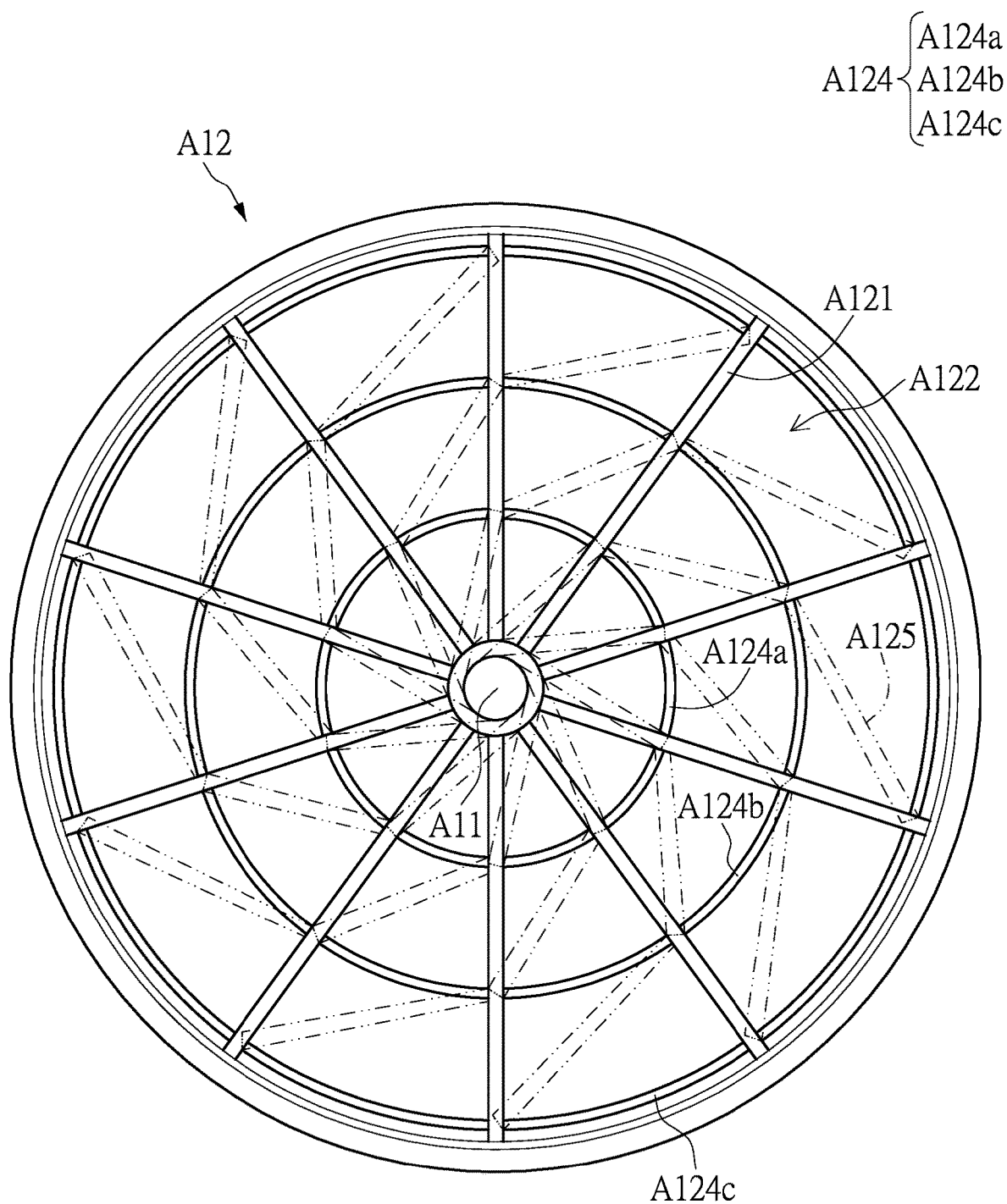
FIG. 2 is a top view of outer rings and ribs mounted on pushing plates according to the first embodiment of the present disclosure.
Figure 3:
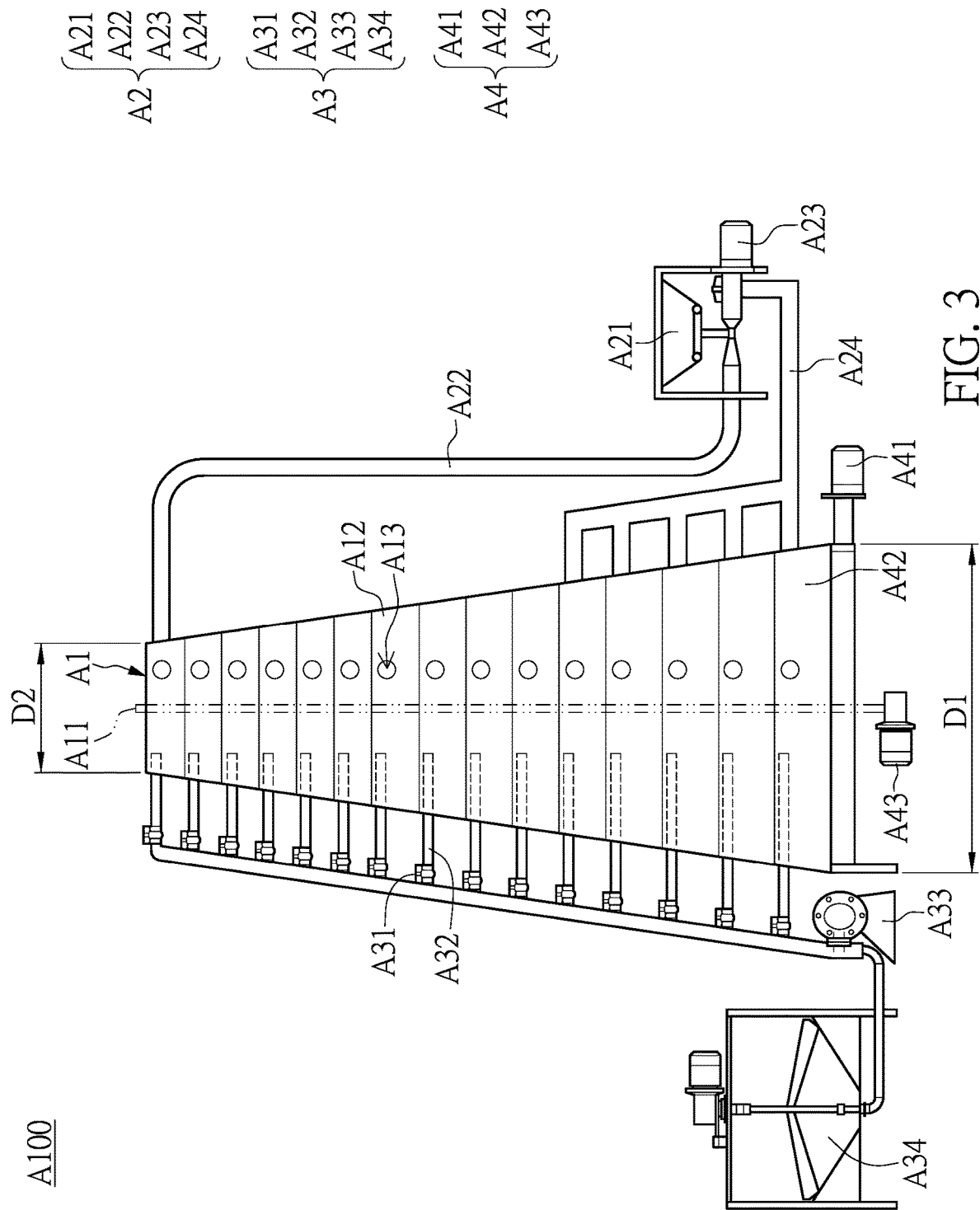
FIG. 3 is a schematic view of a breeding apparatus according to the first embodiment of the present disclosure.

Referring to FIG. 1 to FIG. 3, FIG. 1 is a perspective view of a plurality of rotating disc type breeding boxes according to a first embodiment of the present disclosure, FIG. 2 is a top view of outer rings and ribs mounted on pushing plates according to the first embodiment of the present disclosure, and FIG. 3 is a schematic view of a breeding apparatus according to the first embodiment of the present disclosure.

A first embodiment of the present disclosure provides a rotating disc type continuous automated biological breeding apparatus A100, which can be applied to garbage collection sites or large-scale livestock farms, and used as a large-scale biological breeding apparatus to achieve the purpose of processing a large amount of organic waste. The rotating disc type continuous automated biological breeding apparatus A100 of the present disclosure can stably process organic waste every day in an automated manner, and can efficiently produce black soldier fly as fodder and insect dung as organic fertilizer. The size of the breeding apparatus can be flexibly adjusted according to a total amount of waste to be processed daily. A plurality of rotating disc type breeding boxes A12 of the first embodiment can be designed in different sizes according to the space required for the growth period of the organism. The organisms at an early breeding stage are smaller in size, and their accumulated excrement is also less, so that a smaller rotating disc type breeding box A12 can be used. Subsequently, the organisms gradually grow up, and the accumulated excrement gradually increases, so that a larger rotating disc type breeding box A12 can be used. The plurality of rotating disc type breeding boxes A12 can be stacked upwards in the longitudinal direction from a large size to a small size so as to form a breeding tank A1 that is cone-shaped.

The breeding tank A1 that is cone-shaped is formed by stacking the plurality of rotating disc type breeding boxes A12 on each other in the longitudinal direction, which are defined as different breeding layers to provide an organism growth and breeding platform, and separates organisms of different growth periods. The organisms of different growth periods are bred in the same breeding tank A1 to achieve continuous and automated production. Each of the rotating disc type breeding boxes A12 includes a plurality of pushing plates A121 arranged therein. Any two adjacent pushing plates A121 surround a breeding space, which is called a breeding compartment A122.

A central rotating shaft A11 is disposed at the center of the breeding tank A1 that is cone-shaped. The central rotating shaft A11 penetrates through the plurality of rotating disc type breeding boxes A12. The central rotating shaft A11 is connected to a motor A43 of the breeding apparatus. Each of the pushing plates A121 is connected to the central rotating shaft A11 of the breeding tank A1 that is cone-shaped. When the central rotating shaft A11 rotates along a first rotation direction R1 (i.e., clockwise direction), the central rotating shaft A11 drives each of the pushing plates A121 to rotate along the first rotation direction R1 (i.e., clockwise direction), thereby pushing the organisms in the breeding compartments A122 to move along the first rotation direction R1.

Each of the rotating disc type breeding boxes A12 has an opening slot, which is called a lower feeding port A123. The opening positions of the lower feeding ports A123 of the plurality of rotating disc type breeding boxes A12 are arranged in a staggered manner along a second rotation direction R2 (i.e., counterclockwise direction) opposite to the first rotation direction R1. That is, the lower feeding port A123 of the rotating disc type breeding box A12 of a next layer is disposed at a position where the lower feeding port of the rotating disc type breeding box A12 of an upper layer is disposed at and backwards by one breeding compartment A122 along the second rotation direction R2 (i.e., counterclockwise direction). The organisms are discharged from a discharge hole of the rotating disc type breeding box A12 of the lowest layer so that the finished product is harvested. More specifically, in each of the rotating disc type breeding boxes A12, the lower feeding port A123 is formed at a bottom portion of the rotating disc type breeding box A12. The plurality of pushing plates A121 and the bottom portion of the rotating disc type breeding box A12 are of separate constructions from each other. When the plurality of pushing plates A121 are rotated along the first rotation direction R1, the bottom portion and the lower feeding port A123 are fixed in portion relative to the plurality of pushing plates A121.

When the central rotating shaft A11 rotates, the younger organisms located in the rotating disc type breeding box A12 of the upper layer are pushed by the pushing plate A121 from the lower feeding port A123 to fall to the breeding compartment A122 of the next layer. The organisms that are pushed down from the breeding compartment A122 of the upper layer fall into the position where the breeding compartment A122 of the lower layer has been cleared out. The organisms and excrement are bred from the top layer of the breeding tank A1. The organisms and excrement are pushed down layer by layer until the lowest layer by the rotation of the pushing plates A121, at which time the organisms are grown up to be harvested. Each layer of the rotating disc type breeding boxes A12 has N pushing plates A121 that define N breeding compartments A122. Each layer of the rotating disc type breeding boxes A12 has only one lower feeding port A123, which is slightly smaller than the breeding compartment A122. Each of the breeding compartments A122 is arranged at a certain angle, which is 360°/N, similar to that of a fan blade. The value of N can be the number of the pushing plates in each layer.

In some embodiments of the present disclosure, the plurality of rotating disc type breeding boxes A12 can be designed in different quantities and sizes according to the growth period of different organisms or the size of waste to be processed. The plurality of rotating disc type breeding boxes A12 can be stacked from bottom to top. The rotating disc type breeding box A12 at a lower level has a larger diameter for accommodating the amount of growth of the organisms and the accumulation of more feed and excrement, which requires a larger space, but the present disclosure is not limited thereto.

In some embodiments of the present disclosure, a time interval for the rotation of the pushing plates A121 can be adjusted according to the growth rate of the organisms. For example, the pushing plates A121 can rotate once every 1 hour, or can rotate once every 4 hours. A residence time of the organisms in each of the rotating disc type breeding boxes A12 can be adjusted flexibly.

In some embodiments of the present disclosure, if the diameter of the rotating disc type breeding box A12 is too large (i.e., greater than 3 meters), at least one outer ring A124 is mounted on the plurality of pushing plates A121 to fix the plurality of pushing plates A121, and at least one rib A125 is connected between the central rotating shaft A11 and the at least one outer ring A124, so that the pushing plates A121 can rotate smoothly.

As shown in FIG. 2, one end of the rib A125 is connected to a periphery of the central rotating shaft A11. Another end of the rib A125 is extendedly connected to an intersection of a pushing plate A121 and a first outer ring A124a, then connected to an intersection of a next pushing plate A121 and a second outer ring A124b, and further connected to an intersection of still a next pushing plate A121 and a third outer ring A124c, and so on. When the central rotating shaft A11 rotates, the torsion force of the central rotating shaft A11 acts on the pushing plates A121 to rotate the pushing plates A121. The rib A125 generates force acting on the pushing plates A121 from another side of the central rotating shaft A11 to the first outer ring A124a. Furthermore, the portion of the rib A125 connected between the first outer ring A124a and the second outer ring A124b also generates the same force, which is transmitted to another part of the pushing plates A121, and so on. Each pushing plate A121 can receive the torsion force and a plurality of forces, which act on different parts of the pushing plate A121 at the same time, so as to enhance the rotation force of the pushing plate A121 and enable the structure to operate smoothly.

As shown in FIG. 1 and FIG. 3, a specific application of the first embodiment of the present disclosure is to use black soldier flies to treat crushed food waste, for example, using the black soldier flies to treat 500 kilograms of food waste every day. Fifteen layers of rotating disc type breeding boxes A12 are stacked to form the breeding tank A1 that is cone-shaped. Any two adjacent rotating disc type breeding boxes A12 are spaced apart from each other by an interval of 30 centimeters. Each of the rotating disc type breeding boxes A12 includes ten pushing plates A121 fixedly connected to the central rotating shaft A11. Each of the rotating disc type breeding boxes A12 is divided into ten breeding compartments A122 by the ten pushing plates A121, and only one of the ten breeding compartments A122 has a lower feeding port A123.

The breeding tank A1 has a conical shape. Among the fifteen rotating disc type breeding boxes A12 stacked on top of each other, the diameter D1 of the bottom-layer rotating disc type breeding box A12 is 3 meters, and the diameter D2 of the top-layer rotating disc type breeding box A12 is 0.6 meters. The diameters of the plurality of rotating disc type breeding boxes A12 are sequentially reduced from the bottom-layer rotating disc type breeding box to the top-layer rotating disc type breeding box, so as to form a conical shape, which provides a space suitable for the growth of organisms and can enhance the stability of the breeding tank.

5-day-old larvae after hatching are small in size and low in food intake, so the diameter of the top-layer rotating disc type breeding box A12 can be small. The 5-day-old larvae are fed from the top-layer rotating disc type breeding box A12, and are evenly distributed in each of the breeding compartments A122. The central rotating shaft A11 rotates every 2 hours to drive the pushing plates A121 to push the organisms to move along the first rotation direction R1 (i.e., clockwise direction) by one compartment. When the organisms are pushed to the lower feeding port A123, the organisms fall into the breeding compartment A122 of the next layer to continue breeding. In this way, the organisms stay in each of the rotating disc type breeding boxes A12 in the breeding tank A1 that is cone-shaped for 18 hours (i.e., 2 hours multiplied by 9 breeding compartments equals 18 hours). The breeding tank A1 has fifteen rotating disc type breeding boxes in total. The organisms move from the top-layer breeding box down to the discharge port of the bottom-layer breeding box in a layer-by-layer manner. The total growth time of the organisms is two hundred and seventy hours (i.e., eighteen hours multiplied by fifteen boxes equals two hundred and seventy hours), which is approximately eleven days of growth time. At this time, the larvae have grown to a harvestable stage. Accordingly, the space utilization can be optimized. It is worth mentioning that organisms such as larvae are first placed in an organism placement slot A21 of an organism delivery unit A2, and the organisms are fed to the top-layer rotating disc type breeding box A12 of the breeding tank A1 through an operation of a delivery pipe A22 and a blower A23. In addition, a plurality of gas dredge pipes A24 of the organism delivery unit A2 are respectively connected to gas relief valves A13 of the plurality of rotating disc type breeding boxes A12 to release the gas excreted during the growth of the organisms.

The bottom-layer rotating disc type breeding box A12 is used to breed the organisms that have grown up and are ready to be harvested. A partition board of the bottom-layer rotating disc type breeding box A12 is designed as a perforated board A42, and a closed blower A41 is connected below the perforated board. Hot air is blown into the bottom-layer rotating disc type breeding box A12 through the holes of the perforated board to enable gas exchange and drying of the organisms, so that a next stage of screening and separation of the black soldier fly larvae (BSFL) and insect dung can be carried out. The blower A41, the perforated board A42, and the motor A43 constitute a ventilation drying unit A4. The present disclosure can adjust the size, quantity, and spacing of the rotating disc type breeding boxes, and interval time of the rotation of the central rotating shaft according to the amount of organic waste to be processed or the characteristics of the organism to be bred. In addition, the conical rotating disc type breeding tank can also be made into a closed type or an open type with reference to the space or environmental requirements of the breeding site.

Referring to FIG. 3 again, the specific application of the first embodiment of the present disclosure is illustrated by taking the breeding of black soldier flies and the treatment of 500 kilograms of organic waste per day as an example. The breeding tank A1 that is cone-shaped is designed with the bottom-layer breeding box A12 having a diameter D1 of 3 meters and the top-layer breeding box A12 having a diameter D2 of 0.6 meters. In addition, a height of the breeding tank A1 is 4.5 meters. Any two adjacent of the rotating disc type breeding boxes A12 are spaced apart from each other by 30 centimeters. Fifteen layers of the rotating disc type breeding boxes A12 together form the breeding tank A1 that is cone-shaped. 50 grams of black soldier fly larvae on the 5th day after hatching were collected and inoculated evenly in the uppermost breeding compartments A122. Food waste with a moisture content of approximately 70% is introduced into a storage barrel A34 of an automatic feed feeding unit A3, and is sent to the rotating disc type breeding boxes A12 through a coordinated operation of control valves A31, feeding pipelines A32, and a pump A33 of the automatic feed feeding unit A3. The food waste supplies are set differently according to different amounts of the feed intake by larvae at different periods. An electronic control unit is set to enable feeding once every 2 hours. The central rotating shaft A11 is set to rotate once every 2 hours. The ventilation drying unit A4 is activated and set to operate for 5 minutes every 10 minutes. The lower feeding port A123 of the bottom-layer rotating disc type breeding box A12 of the breeding tank A1 that is cone-shaped discharges finished products every 2 hours. The finished products are conveyed by a conveyor belt to an oscillating screening machine for a first screening (not shown in the drawings). The system provided by the present disclosure can process 500 kilograms of food waste per day. The finished products approximately include 150 kilograms of black soldier flies larvae and 200 kilograms of worm dung. The operation of the system generally requires 1 person. In general, when the rotating disc type continuous automated biological breeding apparatus is applied to a large-scale kitchen waste processing device, the organisms that are harvested and cultivated are transported to a vibrating screening machine via an automatic conveyor belt to separate the organisms from excrement of the organisms, the excrement is used as organic fertilizer, and then the organisms undergo a water washing procedure, a retention procedure, a boiling disinfection procedure, a drying procedure, a liposuction procedure, a milling procedure, and a packaging procedure that are automatically carried out.

[Small-Scale Biological Breeding Apparatus]

Figure 4:
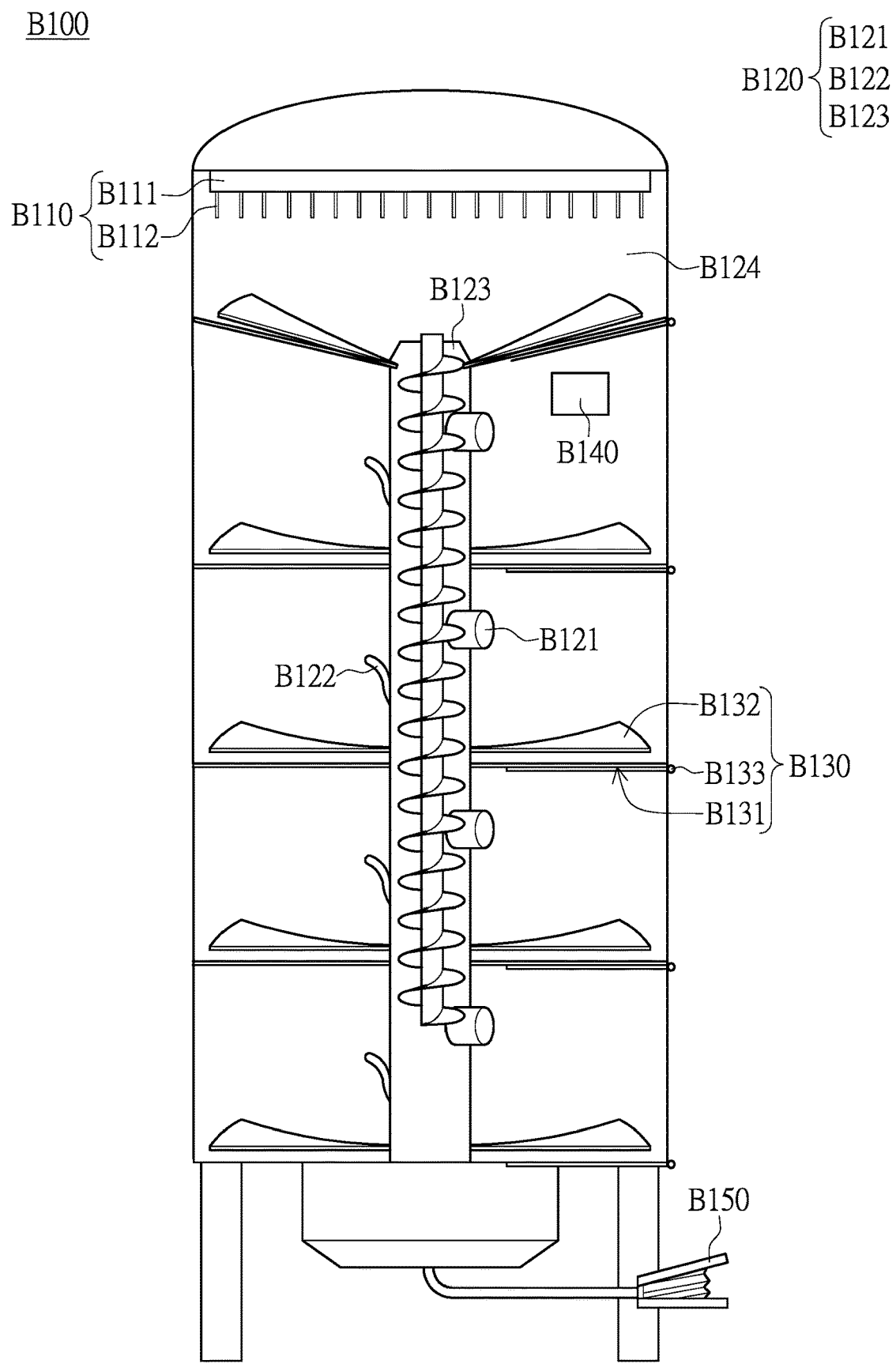
FIG. 4 is a schematic view of a breeding apparatus according to a second embodiment of the present disclosure.

Referring to FIG. 4, a second embodiment of the present disclosure provides a rotating disc type continuous automated biological breeding apparatus B100, which can be used as a small-scale breeding apparatus for kitchen waste in communities or households. In this way, the purpose of on-site and immediate disposal of food waste and organic waste can be achieved.

The rotating disc type continuous automated biological breeding apparatus B100 of the second embodiment is mainly used for processing food waste within 5 kilograms per day. The design concept of the breeding apparatus of the second embodiment is substantially the same as that of the above-mentioned first embodiment. The difference lies in that the breeding apparatus of the second embodiment is a closed cylinder with a diameter of 50 centimeters and a height of 85 centimeters. The appearance of the breeding apparatus is similar to that of a closed trash can, but the present disclosure is not limited thereto.

The rotating disc type continuous automated biological breeding apparatus B100 of the present embodiment includes four rotating disc type breeding boxes B130 that have the same diameter. Each of the rotating disc type breeding boxes B130 has a diameter of 50 centimeters. Each of the rotating disc type breeding boxes B130 includes three pushing plates B132 respectively connected to a central rotating shaft B123. Any two adjacent rotating disc type breeding boxes B130 are spaced apart from each other by 15 centimeters. Furthermore, any two adjacent pushing plates B132 form a grid of breeding space, which is called breeding compartment (not labeled in the drawing). It is worth mentioning that heights of the pushing plates B132 need to be designed to surround the breeding compartment, so that organisms can be accommodated in the breeding compartment, and the organisms can be pushed by the pushing plates B132 and do not fall over the pushing plates B132 into another adjacent breeding compartment. As long as the pushing plates B132 can meet the above design requirements, other structural features (i.e., shape) of the pushing plates are not limited thereto.

A cutting module B110 is disposed under an upper cover of the rotating disc type continuous automated biological breeding apparatus B100 of the present embodiment. The cutting module B110 includes a chopping block B111 and a blade B112 disposed on a lower side of the chopping block B111. The cutting module B110 is used to chop the input food waste, and drop the input food waste into a fermentation tank B124 below the cutting module B110.

The central rotating shaft B123 of the rotating disc type continuous automated biological breeding apparatus B100 of the present embodiment is connected to a foot pedal B150 disposed at the bottom of the breeding apparatus. An inside of the central rotating shaft B123 has a spiral feeding device B120, which includes at least one discharge port B121 for feeding organic waste and at least one air outlet B122 for ventilation. The rotating disc type continuous automated biological breeding apparatus B100 of the present embodiment can carry out a preliminary fermentation of the food waste after preliminary treatment in the fermentation tank B124, and then convey the food waste to the rotating disc type breeding boxes B130 of different layers by the spiral feeding device B120 to provide the black soldier flies or mealworms to feed and grow.

When the breeding apparatus B100 is in use, a user can first open the upper cover of the breeding apparatus B100 to drain off and pour the household kitchen waste onto the blade B112, and then the user can cover the upper cover and step on the foot pedal B150 several times to drive the pushing plates B132 to rotate.

Further, the user can open a lower feeding port B131 of the bottom-layer breeding box B130 every week, and rotate the pushing plate B132 to harvest mature larvae. Feeding port shutters B133 of the lower feeding ports B131 can be opened in sequence, and the foot pedal B150 can be pedaled to rotate the central rotating shaft B123, so that the black soldier flies in each breeding layer fall from the rotating disc type breeding box B130 of an upper layer to the rotating disc type breeding box B130 of an lower layer. The user can inject five-day-old black soldier fly larvae from an inoculation port B140 every week.

The rotating disc type continuous automated biological breeding apparatus B100 of the present embodiment can be placed under a kitchen countertop or on an outdoor balcony, and the rotating disc type continuous automated biological breeding apparatus B100 can continuously and stably use the kitchen waste produced by the household to feed the black soldier flies. The rotating disc type continuous automated biological breeding apparatus B100 of the present embodiment also has supporting measures. A service center can collect mature larvae and insect dung, and supply five-day-old larvae at the same time. The business operation model of the rotating disc type continuous automated biological breeding apparatus B100 of the present embodiment is that the service center is responsible for breeding insects, the recovered mature larvae can be processed into feed, insect dung can be made into organic fertilizer, and proceeds from selling the feed and organic fertilizer can be returned to the user of the breeding apparatus, so as to achieve the purpose of a sharing economy. In other words, when the breeding apparatus is applied to a small-scale community food waste processor or a household food waste processor, a business operation model includes setting up a joint service center to supply early-age organisms, to recycle aging organisms, and to return profits to users.

Referring to FIG. 4 again, the specific application of the second embodiment is illustrated by taking the breeding of black flies and the treatment of food waste below 5 kilograms per day as an example. The breeding tank is designed to have a diameter of 0.5 meters and a height of 0.8 meters. One layer of the rotating disc type breeding box B130 is designed every 15 centimeters inside the breeding tank, and 5 layers in total are designed to form the breeding tank. After the food waste passes through the upper cover of the breeding device B100 and is broken by the cutting module B110, the food waste enters the fermentation tank and is distributed to each breeding layer through the spiral feeding device B120.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A rotating disc type continuous automated biological breeding apparatus, comprising:
   a plurality of rotating disc type breeding boxes stacked on each other in a longitudinal direction to form a breeding tank; wherein each of the rotating disc type breeding boxes includes at least one pushing plate and a lower feeding port, and the at least one pushing plate is configured to divide one of the rotating disc type breeding boxes that corresponds to the at least one pushing plate into at least one breeding compartment; and
   a central rotating shaft penetrating through the plurality of rotating disc type breeding boxes in the longitudinal direction; wherein a plurality ones of the pushing plates of the plurality of rotating disc type breeding boxes are fixedly connected to the central rotating shaft, and the central rotating shaft is configured to drive the plurality ones of the pushing plates of the plurality of rotating disc type breeding boxes to rotate in a first rotation direction through a motor or a pedal;
   wherein a top-layer breeding box of the plurality of rotating disc type breeding boxes is configured to receive organisms to be cultivated; wherein, when the central rotating shaft drives the plurality ones of the pushing plates of the plurality of rotating disc type breeding boxes to rotate, the organisms located in the top-layer breeding box are pushed by the at least one pushing plate into the at least one breeding compartment of a second-layer breeding box of the plurality of rotating disc type breeding boxes below the top-layer breeding box through the lower feeding port of the top-layer breeding box, and then the organisms are pushed into the at least one breeding compartment of a third-layer breeding box of the plurality of rotating disc type breeding boxes below the second-layer breeding box through the lower feeding port of the second-layer breeding box until the organisms are pushed into a bottom-layer breeding box of the plurality of rotating disc type breeding boxes, so as to complete a cultivation process of the organisms.

2. The rotating disc type continuous automated biological breeding apparatus according to claim 1, wherein the lower feeding ports of the plurality of rotating disc type breeding boxes are arranged to be staggered with each other along a second rotation direction opposite to the first rotation direction, any two adjacent ones of the lower feeding ports are staggered by a predetermined angle of $360°/n$, and n is a quantity of the plurality of rotating disc type breeding boxes.

3. The rotating disc type continuous automated biological breeding apparatus according to claim 1, wherein the lower feeding port of each of the rotating disc type breeding boxes and the at least one breeding compartment of the rotating disc type breeding box of a next layer are staggered with each other and arranged on different vertical planes.

4. The rotating disc type continuous automated biological breeding apparatus according to claim 1, wherein a diameter of the bottom-layer breeding box is greater than a diameter of the top-layer breeding box, and diameters of the plurality of rotating disc type breeding boxes gradually increase from the top-layer breeding box to the bottom-layer breeding box so that the breeding tank has a conical shape.

5. The rotating disc type continuous automated biological breeding apparatus according to claim 1, wherein, in each of the rotating disc type breeding boxes, a quantity of the at least one of pushing plate is at least two; wherein a diameter of one of the rotating disc type breeding box is greater than 3 meters, the rotating disc type breeding box further includes a first outer ring, a second outer ring, and at least one rib; wherein the first outer ring and the second outer ring are mounted on the at least two pushing plates, the at least one rib is fixedly connected to the central rotating shaft and is extendedly connected to an intersection of one of the pushing plates and the first outer ring, and the at least one rib is further connected to an intersection of another one of the pushing plates and the second outer ring.

6. The rotating disc type continuous automated biological breeding apparatus according to claim 1, wherein the organisms to be cultivated are black soldier flies, house flies, mealworms, crickets, *Spodoptera litura*, silkworms, cockroaches, soil beetles, lacewings, rice worms, beetles, earthworms, microorganisms, aquaculture organisms, or other creatures capable of being used for bred or being consumed by natural enemies.

7. The rotating disc type continuous automated biological breeding apparatus according to claim 1, wherein the breeding tank is configured to receive a feed, and the feed is at least one of kitchen waste, fruit and vegetable residues, distiller grains, bean dregs, tea residues, coffee residues, poultry and livestock manures, slaughterhouse waste, animal carcasses, food factory waste, sludges, biogas muds, and other organic wastes.

* * * * *